(12) United States Patent
Hodin et al.

(10) Patent No.: US 8,932,587 B2
(45) Date of Patent: Jan. 13, 2015

(54) METHODS OF REDUCING OR INHIBITING TOXIC EFFECTS ASSOCIATED WITH A BACTERIAL INFECTION USING ALKALINE PHOSPHATASE

(75) Inventors: Richard A. Hodin, Newton, MA (US); Madhu S. Malo, Burlington, MA (US)

(73) Assignee: The General Hospital Corporation, Boston, MA (US)

( * ) Notice: Subject to any disclaimer, the term of this patent is extended or adjusted under 35 U.S.C. 154(b) by 49 days.

(21) Appl. No.: 13/578,103

(22) PCT Filed: Feb. 11, 2011

(86) PCT No.: PCT/US2011/024521
§ 371 (c)(1), (2), (4) Date: Oct. 5, 2012

(87) PCT Pub. No.: WO2011/100543
PCT Pub. Date: Aug. 18, 2011

(65) Prior Publication Data
US 2013/0022591 A1    Jan. 24, 2013

(51) Int. Cl.
*A61K 38/46* (2006.01)
*A61K 31/74* (2006.01)

(52) U.S. Cl.
CPC ............... *A61K 31/74* (2013.01); *A61K 38/465* (2013.01); *C12Y 301/03001* (2013.01)
USPC ......................................... 424/94.6; 435/196

(58) Field of Classification Search
CPC ..... A61K 31/74; A61K 38/465; A61K 45/06; A61K 39/3955; A61K 31/00; A61K 38/28; A61K 2300/00; C12Y 301/03001; C12N 9/16
See application file for complete search history.

(56) References Cited

U.S. PATENT DOCUMENTS

| | | | |
|---|---|---|---|
| 6,290,952 | B1 | 9/2001 | Poelstra et al. |
| 2007/0059300 | A1* | 3/2007 | Kiss .............................. 424/94.6 |

FOREIGN PATENT DOCUMENTS

| | | |
|---|---|---|
| EP | 1 952 823 | 8/2008 |
| WO | 2004/112494 | 12/2004 |
| WO | WO 2005074978 A1 * | 8/2005 |
| WO | 2008/104200 | 9/2008 |
| WO | 2010/025267 | 3/2010 |

OTHER PUBLICATIONS

Beumer C., Calf Intestinal Alkaline Phosphatase, a Novel Therapeutic Drug for Lipopolysaccharide (LPS)-Mediated Diseases, Attenuates LPS Toxicity in Mice and Piglets, The Journal of Pharmacology and Experimental Therapeutics, 2003, vol. 307, No. 2, pp. 737-744.*
Medscape General Surgery 2007: "Shifting Sands in Surgical Dogma: Evidence-Based Reappraisal of Perioperative Practices", American College of Surgeons, 93rd Annual Clinical Congress, Session GS52, on the web at http://www.medscape.org/viewarticle/568029, pp. 1-5.*
NIH Clinical Guideline—"Surgical site infection: prevention and treatment of surgical site infection", National Collaborating Centre for Women's and Children's Health, Oct. 2008, pp. 1-142 (Commissioned by the National Institute for Health and Clinical Excellence, and Published by the RCOG Press, London).*
Bates et al., "Intestinal alkaline phosphatase detoxifies lipopolysaccharide and prevents inflammation in zebrafish in response to the gut microbiota," Cell Host Microbe, 2(6):371-82 (Dec. 2007).
Chavarii et al., "Alkaline Phosphatase, Acid Phosphatase, Lactoperoxidase, and Lipoprotein Lipase Activities in Industrial Ewe's Milk and Cheese," J. Agric. Food Chem., 46:2926-2932 (1998).
Ebrahimi et al., "Local Peritoneal Irrigation with Intestinal Alkaline Phosphatase Is Protective Against Peritonitis in Mice," J. Gastrointest. Surg., 15:860-869 (2011).
European Communication; Application No. 09810593.5-2107; mailed May 30, 2012; Applicant: The General Hospital Corporation; 3 pages.
European Office Action; Application No. 09810593.5-2107; mailed Jun. 13, 2012; Applicant: The General Hospital Corporation; 5 pages.
Flegel et al., "Cytokine response by human monocytes to Clostridium difficile toxin A and toxin B," Infection and Immunity, 59(10):3659-3666 (1991).
International Search Report and Written Opinion dated Mar. 24, 2010 issued in International Application No. PCT/US2009/055216, 12 pgs.
International Search Report and Written Opinion issued in PCT/US2011/024521 dated Oct. 25, 2011 (5 pages).
McFarland, Lynne V., "Alternative treatments for Clostridium difficile disease: what really works?" Journal of Medical Microbiology, 54:101-111 (2005).
Rozenfeld et al., The Role of Intestinal Flora in Endotoxin (LPS)-Induced Gut Injury and Group II Phospholipase A2 (PLA2-11) Activation in the Small Intestine. Pediatric Research, 45(4): 45A (Apr. 1999). See abstracts.
Vaishnava et al., "Alkaline Phosphatase: Keeping the Peace at the Gut Epithelial Surface," Cell Host Microbe, 2(6): 365-67 (Dec. 2007).
Bochud et al., "Antimicrobial therapy for patients with severe sepsis and septic shock: An evidence-based review," Crit. Care Med., 32[Suppl]:S495-S512 (2004).
Cohen et al., "The immunopathogenesis of sepsis," Nature, 40:885-891 (2002).
European Communication; Application No. 09810593.5-1456; mailed May 14, 2013; Applicant: The General Hospital Corporation; 5 pages.
Extended European Search Report; Application No. 11742861.5; mailed Jun. 6, 2013; Applicant: The General Hospital Corporation; 8 pages.
Final Office Action issued in U.S. Appl. No. 13/060,863 on Apr. 25, 2013 (12 pages).
Fish & Richardson P.C. RCE and Response to Office Action issued in U.S. Appl. No. 13/060,863 on Apr. 25, 2013 filed on Jul. 22, 2013 (11 pages).
Fish & Richardson P.C. Response to Office Action issued in EP09810593.5 on Jun. 13, 2012 filed on Dec. 19, 2012 (7 pages).
Fish & Richardson P.C. Response to Office Action issued in EP11742861.5 on Jun. 25, 2013 filed on Jan. 6, 2014 (7 pages).
Fish & Richardson P.C. Response to Office Action issued in U.S. Appl. No. 13/060,863 Nov. 8, 2012 filed on Apr. 25, 2013 (10 pages).

(Continued)

*Primary Examiner* — Satyendra Singh
(74) *Attorney, Agent, or Firm* — Fish & Richardson P.C.

(57) ABSTRACT

This invention relates generally to a therapeutic use of alkaline phosphatase to reduce or inhibit toxic effects associated with a bacterial infection in a subject.

9 Claims, 11 Drawing Sheets

(56) References Cited

OTHER PUBLICATIONS

Klaas et al., "A single injection of alkaline phosphatase significantly attenuates the inflammatory response upon lipopolysaccharide (LPS) in serum and in livers of mice," Database BIOSIS [Online] Biosciences Information Service, Philadelphia, PA & Hepatology, 34(4): 279A, 52nd Annual Meeting and Postgraduate Courses of the American Association for the Study of Liver Disease, Dallas, TX (2001).

Office Action issued in U.S. Appl. No. 13/060,863 on Nov. 8, 2012 (14 pages).

Office Action issued in U.S. Appl. No. 13/060,863 on Oct. 4, 2013 (10 pages).

Platell et al., "Acute Pancreatitis: Effect of Somatostatin Analogs and Peritoneal Lavage," Journal of Gastroenterology and Hepatology, 16:689-693 (2001).

Platell et al., "The Influence of Lavage on Peritonitis," J. Am. Coll. Surg., 191(6):672-680 (2000).

Van Veen et al., "Bovine intestinal alkaline phosphatase attenuates the inflammatory response in secondary peritonitis in mice," Infection and Immunity, American Society for Macrobiology, 73(7):4309-4314 (2005).

Whiteside et al., "Intra-operative peritoneal lavage—who does it and why?" Ann. R. Coll. Surg. Engl., 87:255-258 (2005).

\* cited by examiner

METHODS OF REDUCING OR INHIBITING TOXIC EFFECTS ASSOCIATED WITH A BACTERIAL INFECTION USING ALKALINE PHOSPHATASE

FEDERALLY SPONSORED RESEARCH OR DEVELOPMENT

This invention was made with Government support under Grant Number 2R01DK050623-10A2 awarded by the National Institute of Diabetes and Digestive and Kidney Diseases. The Government has certain rights in the invention.

CROSS REFERENCE TO RELATED APPLICATIONS

This application is a U.S. National Phase Application under 35 U.S.C. §371 of International Application No. PCT/US2011/024521, filed on Feb. 11, 2011, which claims priority from U.S. Application No. 61/303,942, filed on Feb. 12, 2010, both of which are incorporated herein by reference in their entireties.

TECHNICAL FIELD

This invention relates to methods of reducing or inhibiting toxic effects associated with a bacterial infection using alkaline phosphatase.

BACKGROUND

Laparotomy is a surgical procedure involving an incision through the abdominal wall to gain access into the abdominal cavity. Also known as coeliotomy, this procedure is performed for various clinical conditions, including appendicitis, intestinal perforation, liver cancer, stomach cancer, colon cancer, trauma, and sepsis. In addition to the general risks of surgery and the risks of anesthesia, a laparotomy poses its own risks. The risks vary based upon the underlying problem or disease that makes the procedure necessary, but the risks specific to the procedure are infection, incisional hernia, and bleeding from the surgery site. Infection is the most common complication, which often leads to morbidity and mortality.

Peritoneal irrigation with recently available therapeutic agents, including antibiotics and iodine, has limited efficacy. Antibacterial agents may prevent infection, but increase adhesion and do not affect survival rates (Falagas and Vergidis, Clin Microbiol Infect 11:862-867, 2005), most probably due to toxemia from bacterial toxins including lipopolysaccharides (LPS), CpG DNA, and flagellin. Therefore, more effective methods to reduce or inhibit toxic effects associated with a bacterial infection would be desirable.

SUMMARY

This invention is based, at least in part, on the discovery that administering an alkaline phosphatase, e.g., an intestinal, placental, tissue non-specific, or germ-line alkaline phosphatase, to a subject in a therapeutically effective amount, can detoxify bacterial toxins such as lipopolysaccharides, CpG DNA, and flagellin, and can thus safely and easily reduce morbidity and mortality in subjects undergoing laparotomy with little or no side effects. The new methods are effective for a variety of subjects including mammals, e.g., humans and other animals, such as laboratory animals, e.g., mice, rats, rabbits, or monkeys, or domesticated and farm animals, e.g., cats, dogs, goats, sheep, pigs, cows, or horses.

In one aspect, the invention features methods of reducing or inhibiting toxic effects of a bacterial infection in an affected area (i.e., an area affected by an infection or a potential infection) of a subject by administering to the subject a therapeutically effective amount of alkaline phosphatase.

In some embodiments, the affected area is an open wound (e.g., as a result of a surgical procedure or traumatic injury), a body cavity (e.g., peritoneum, sinus, oral, ocular, ear), or an exposed tissue (e.g., skin (e.g., acne, boils, burns), mucosal tissue, eye).

The methods can include administering alkaline phosphatase by irrigation of the affected area.

The methods can also include administering alkaline phosphatase topically to the affected area.

In some embodiments, the methods include administering alkaline phosphatase at or at about the same time as (e.g., concurrent with) a surgical procedure, or at about the same time as, or as soon as possible after, the subject suffers a traumatic injury, e.g., within 2, 4, 6, 8, 10, 12, 24, 48, 96 hours or more.

In some embodiments, the methods also include administering an antibiotic, e.g., before, at the same time, or after the alkaline phosphatase is administered.

In these new methods, the amount of alkaline phosphatase administered can be, for example, from about 1 to about 10,000 units, e.g., 1 to 200; 200 to 500; 500 to 1,000; 1,000 to 5,000; or 5,000 to 10,000 units. Higher doses, e.g., 10,000 to 50,000 units, are also possible. These dosages can be administered over one or more hours or days.

In some embodiments, the amount of alkaline phosphatase administered can be, for example, from about 1 to about 10,000 units/ml, e.g., 1 to 200; 200 to 500; 500 to 1,000; 1,000 to 5,000; or 5,000 to 10,000 units/ml. Higher doses, e.g., 10,000 to 50,000 units/ml, are also possible. These dosages can be administered over one or more hours or days.

The invention provides several advantages. Laparotomy often leads to the development of serious complications, including bacterial infections. The prophylactic and therapeutic methods described herein using an alkaline phosphatase are effective in reducing or inhibiting toxic effects associated with a bacterial infection and have minimal, if any, side effects. These methods provide a desirable treatment option to decrease morbidity and mortality of subjects with open wounds, e.g., subjects undergoing laparotomy.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features, objects, and advantages of the invention will be apparent from the detailed description, and from the claims.

Figure 2:
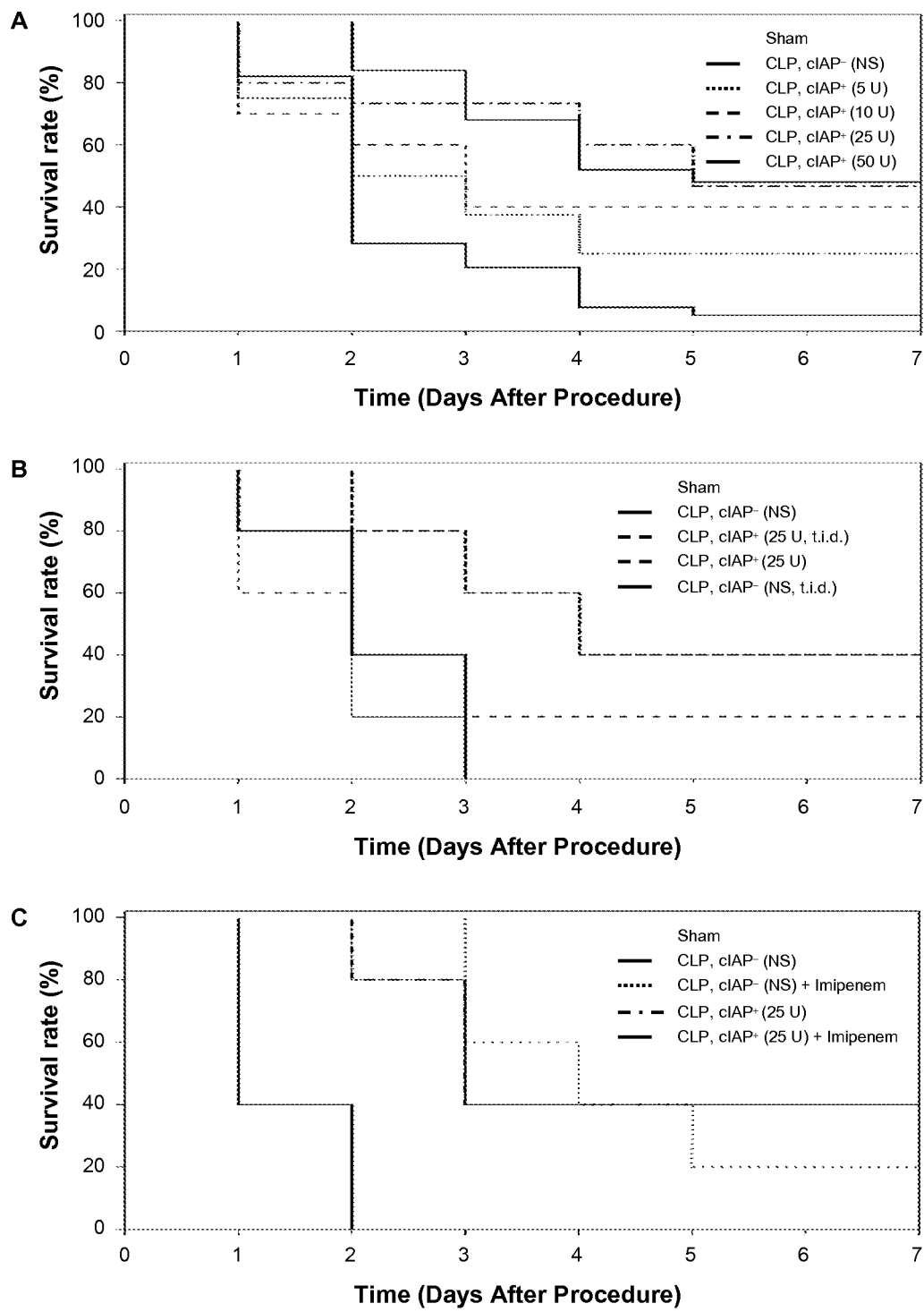

FIG. 2. (A) Dose-response effects of cIAP on the survival of mice with cecal ligation and puncture (CLP). Each animal of a group (n=12 per group) received a single i.p. injection of a specific amount of cIAP (5, 10, 25, or 50 units). cIAP was diluted in normal saline (NS, 0.9% sodium chloride). The control group received a single i.p. injection of NS. All animals received the same volume of i.p. injection (200 μl). The animals were observed for 7 days. (B) Survival rate in CLP mice treated with a single injection of cIAP (25 units), multiple injections of cIAP (25 units, t.i.d.) or NS. (C) Survival rate in CLP mice treated with NS, cIAP (25 units), imipenem (500 μg, b.i.d) or co-administration of cIAP and imipenem.

Figure 3:
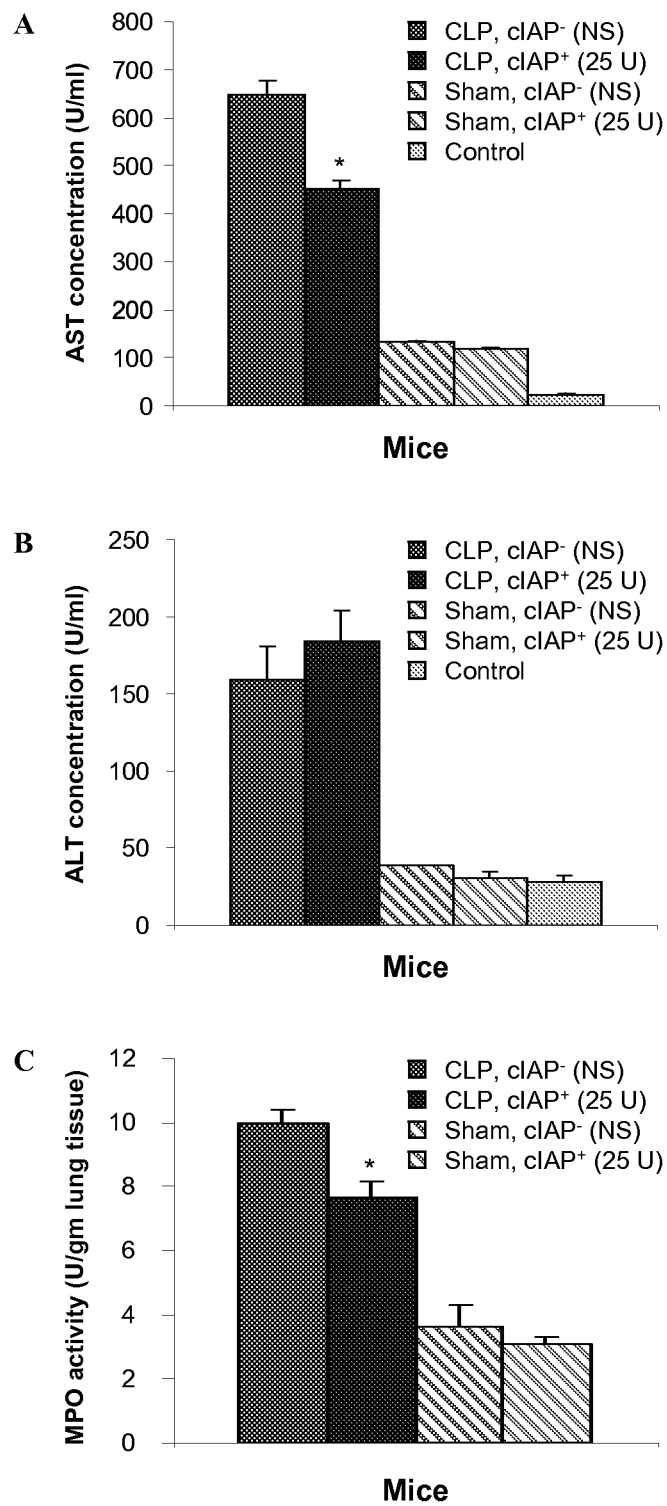

FIG. 3. Effects of cIAP treatment on damages of distal organs by CLP. CLP was performed and the animal was treated with or without cIAP (25 U). Twenty-four hours after CLP, plasma levels of liver enzymes (AST, ALT) were determined. Remote inflammatory response in the lung was assessed by measuring myeloperoxidase (MPO) activity. (A) Plasma levels of AST. (B) Plasma levels of ALT. (C) MPO activity in lung homogenates. Values are expressed as mean+/−SD. *, statistically significant ($p<0.05$).

Figure 4:
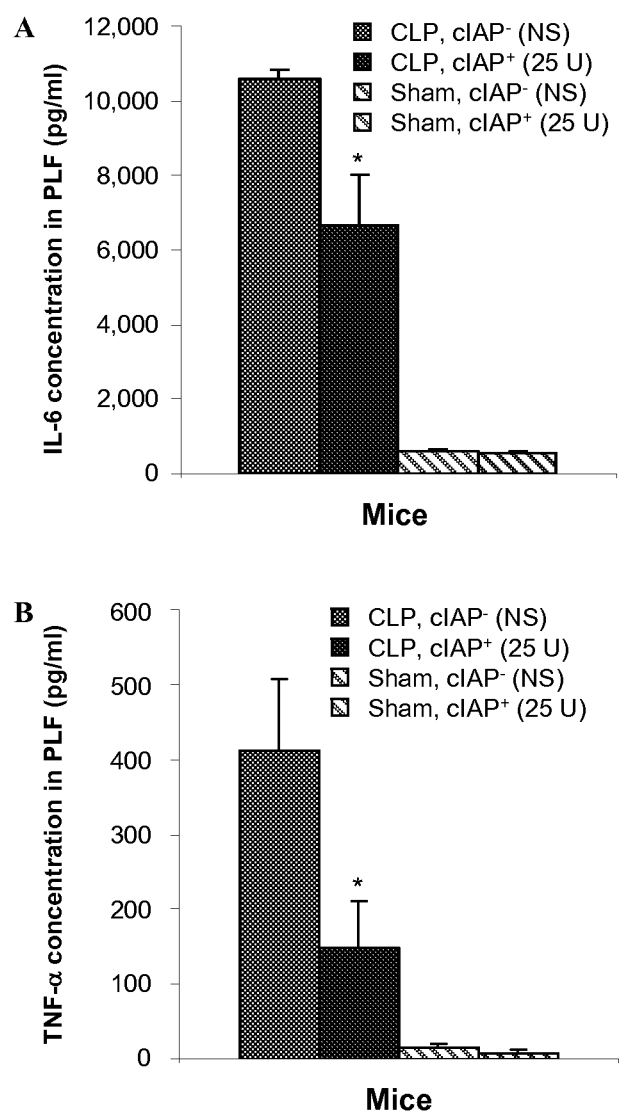

FIG. 4. Effects of cIAP treatment on local cytokine responses during secondary peritonitis. Mice were subjected to secondary peritonitis by CLP and were given cIAP (25 Units) or normal saline (NS, 0.9% sodium chloride). Sham treated mice received cIAP or NS. Proinflammatory cytokine levels were determined in the peritoneal lavage fluid (PLF) 24 hours after CLP or sham operation. (A) Levels of IL-6. (B) Levels of TNF-α. Values are expressed as mean+/−SD. *, statistically significant ($p<0.05$).

Figure 5:
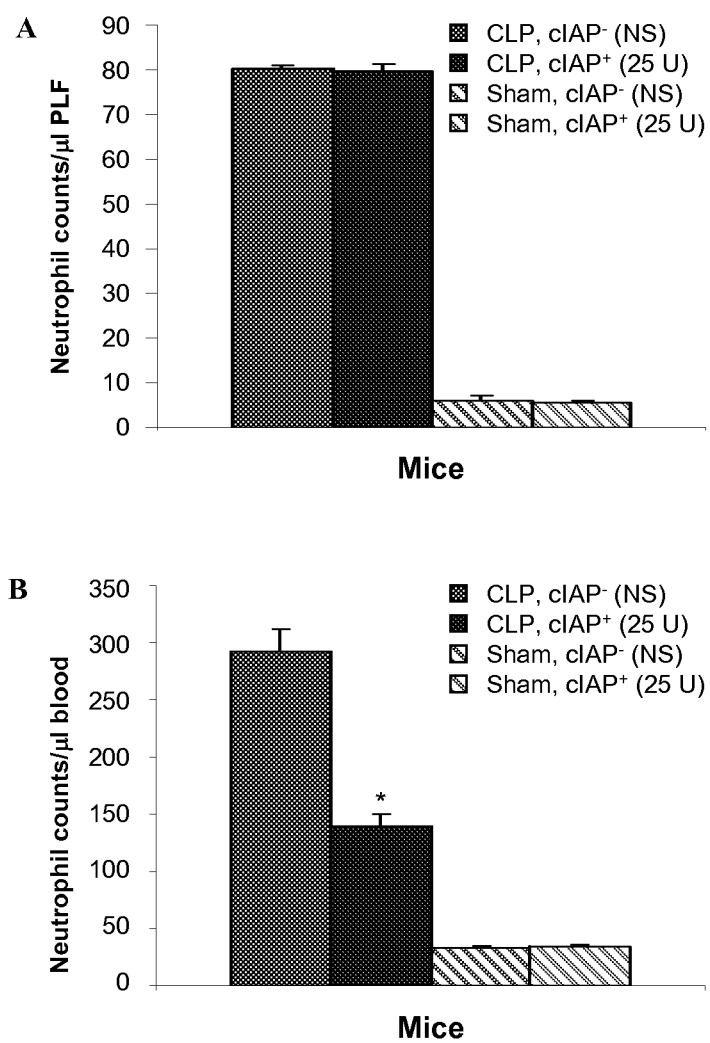

FIG. 5. Effects of cIAP treatment on systemic and local neutrophil responses to secondary peritonitis. Mice were subjected to secondary peritonitis by CLP and were given cIAP (25 Units) or normal saline (NS, 0.9% sodium chloride). Sham treated mice received cIAP or NS. Neutrophil counts per one μA PLF or blood were determined 24 hours after CLP or sham operation. (A) Neutrophil counts in PLF. (B) Neutrophil counts in blood. Values are expressed as mean+/−SD. *, statistically significant ($p<0.05$).

Figure 6:
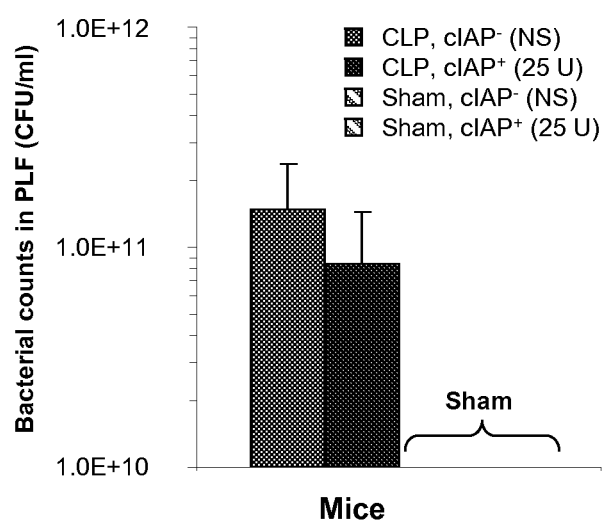

FIG. 6. Effects of cIAP treatment on peritoneal bacterial counts in mice with secondary peritonitis. Peritoneal lavage fluid (PLF) samples from CLP or sham mice were plated in *Brucella* agar in aerobic conditions. Plates were incubated at 37° C. for overnight and CFU/ml of PLF were calculated. Values are expressed as mean+/−SD ($p<0.05$). Note: The bacterial counts were lower in the cIAP-treated CLP animals compared to untreated animals, but the difference was not statistically significant. PLF of animals treated with sham operation did not contain any bacteria.

Figure 7:
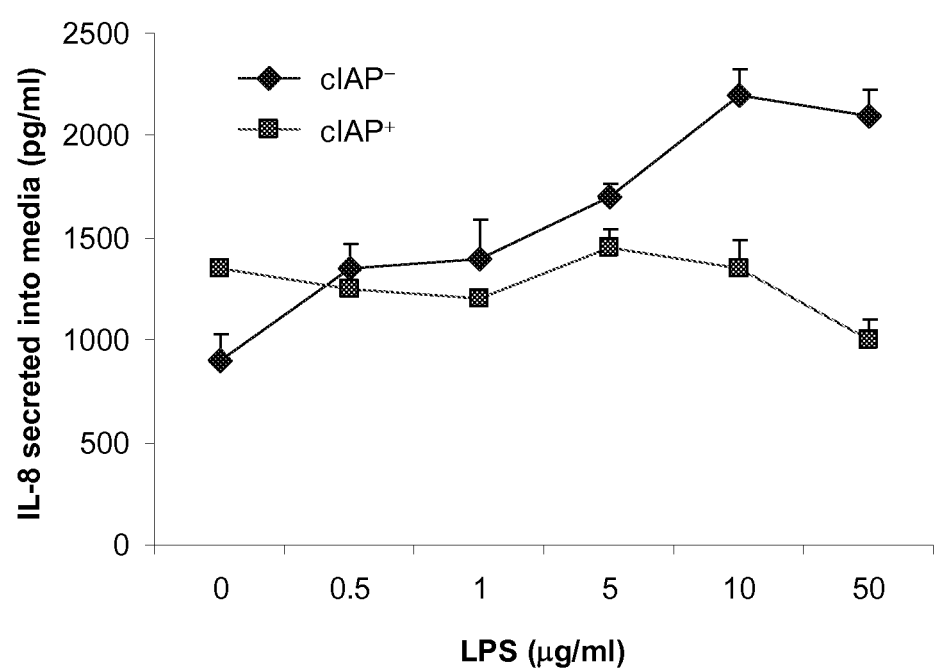

FIG. 7. Effects of cIAP treatment on bacterial lipopolysaccharides (LPS)-induced production of proinflammatory cytokine interleukin-8 (IL-8) in HT29 cells. Various amounts of *E. coli* LPS were incubated at 37° C. with or without cIAP (100 units/ml) for 2 hours. The solutions were then directly applied to HT29 cells (approximately $10^6$ cells in 500 μl, 12-well plates) for 24 hours at 37° C. Media was collected and centrifuged, and the supernatant was assayed for IL-8 content by ELISA. Values are expressed as mean+/−SD. *, statistically significant ($p<0.05$).

Figure 8:
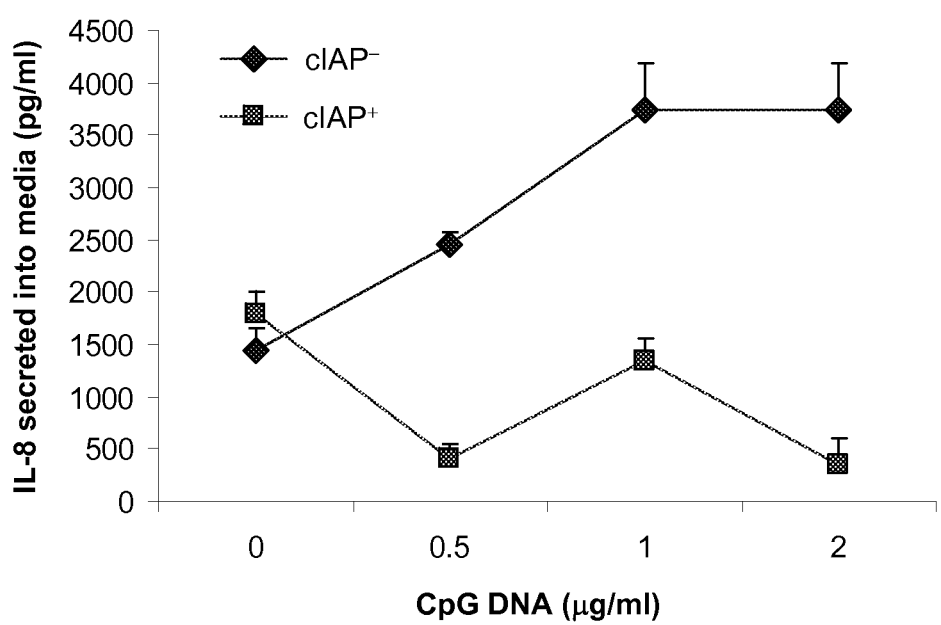

FIG. 8. Effects of cIAP treatment on bacterial CpG DNA-induced production of proinflammatory cytokine interleukin-8 (IL-8) in HT29 cells. Various amounts of CpG DNA were incubated at 37° C. with or without cIAP (100 units/ml) for 2 hours. The solutions were then directly applied to HT29 cells (approximately $10^6$ cells in 500 μl, 12-well plates) for 24 hours at 37° C. Media was collected and centrifuged, and the supernatant was assayed for IL-8 content by ELISA. Values are expressed as mean+/−SD. *, statistically significant ($p<0.05$).

Figure 9:
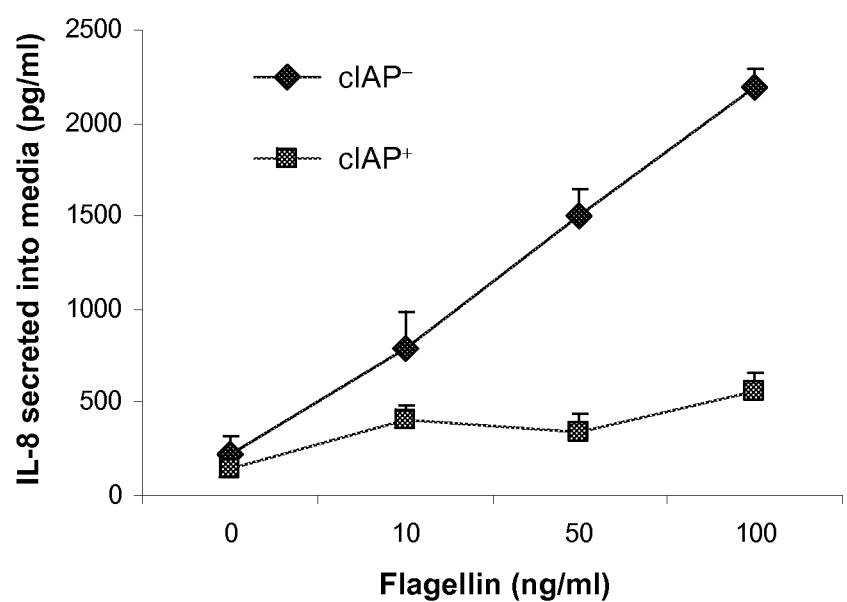

FIG. 9. Effects of cIAP treatment on bacterial flagellin-induced production of proinflammatory cytokine interleukin-8 (IL-8) in THP-1 cells. Various amounts of *Salmonella* flagellin were incubated at 37° C. with or without CIP (100 units) for 16 hours. The flagellin solutions were then mixed with undifferentiated THP-1 monocyte cells (approximately $10^5$ cells in 250 μl), seeded into 48-well plates, and incubated for 24 hours at 37° C. Media was collected and centrifuged, and the supernatant was assayed for IL-8 content by ELISA. Values are expressed as mean+/−SD ($p<0.05$). *, statistically significant ($p<0.05$).

Figure 10:
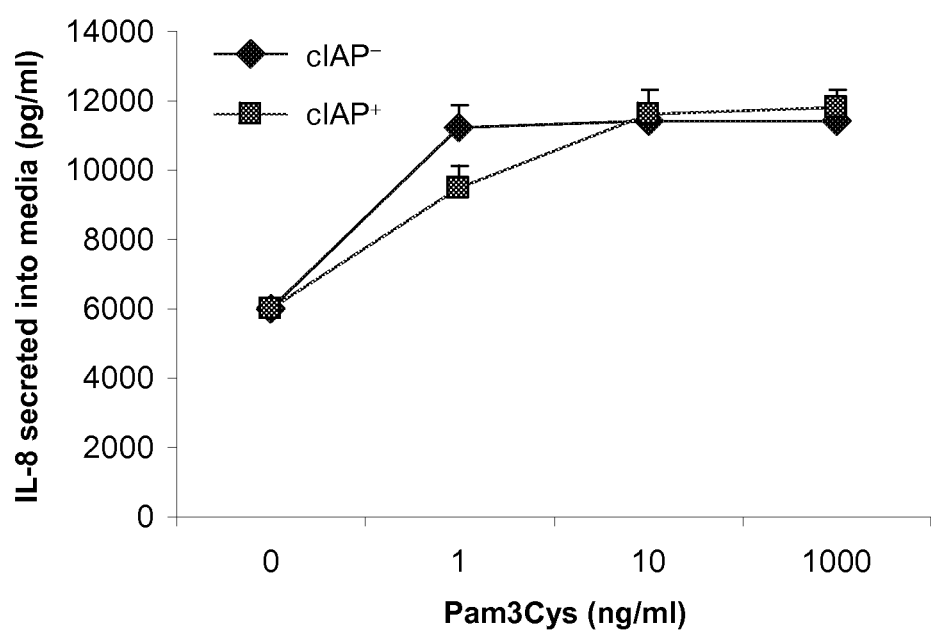

FIG. 10. Effects of cIAP treatment on Pam3Cys-induced production of proinflammatory cytokine interleukin-8 (IL-8) in THP-1 cells. Various amounts of Pam3Cys were incubated at 37° C. with or without CIP (100 units) for 2 hours. The Pam3Cys solutions were then mixed with differentiated THP-1 monocyte cells (approximately $10^6$ cells in 500 μl, 12-well plates) and incubated for 24 hours at 37° C. Media was collected and centrifuged, and the supernatant was assayed for IL-8 content by ELISA. Values are expressed as mean+/−SD. *, statistically significant ($p<0.05$).

Figure 11:
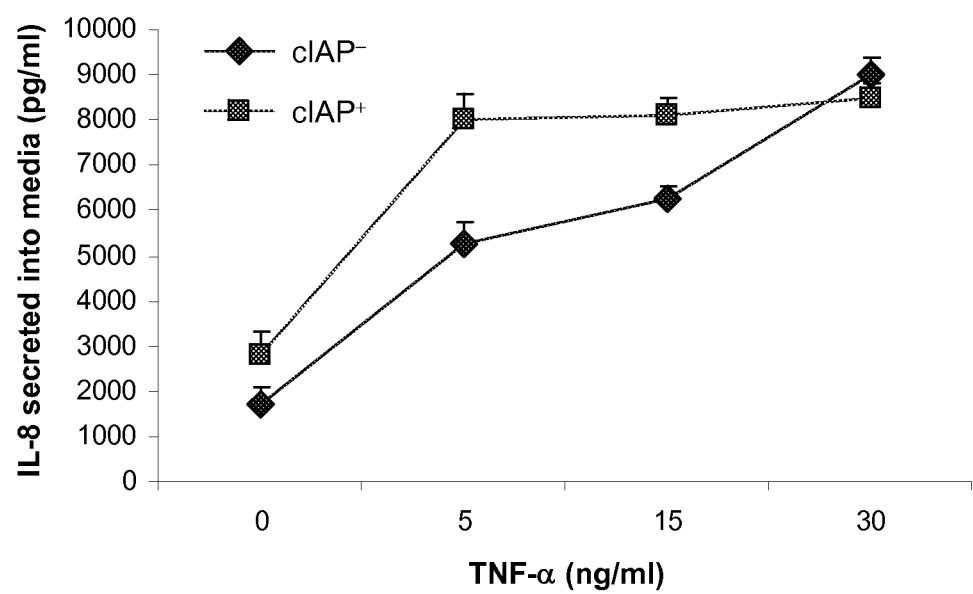

FIG. 11. Effects of cIAP treatment on TNF-α-induced production of proinflammatory cytokine interleukin-8 (IL-8) in HT29 cells. Various amounts of TNF-α were incubated at 37° C. with or without cIAP (100 units/ml) for 2 hours. The TNF-α solutions were then directly applied to HT29 cells (approximately $10^6$ cells in 500 μl, 12-well plates) for 24 hours at 37° C. Media was collected and centrifuged, and the supernatant was assayed for IL-8 content by ELISA. Values are expressed as mean+/−SD. *, statistically significant ($p<0.05$).

DETAILED DESCRIPTION

A bacterial infection is one of the most common complications of an open wound. Provided herein are methods for reducing or inhibiting toxic effects of a bacterial infection in an open wound in a subject by treating the subject with an alkaline phosphatase in an amount effective to reduce or inhibit the toxic effects. An open wound is a type of injury in which skin is torn, cut, or punctured and can be classified according to the object that caused the wound. Incisions or incised wounds are caused by a clean, sharp-edged object such as a knife, razor, or glass splinter. Lacerations are irregular tear-like wounds caused by some blunt trauma. Abrasions are superficial wounds in which the topmost layer of the skin (i.e., the epidermis) is scraped off. Abrasions are often caused by a sliding fall onto a rough surface. Puncture wounds are caused by an object puncturing the skin, such as a nail or needle. Penetration wounds are caused by an object such as a knife entering the body. Gunshot wounds are caused by a bullet or similar projectile driving into or through the body. There may be two gunshot wounds, one at the site of entry and one at the site of exit.

General Methodology

The methods described herein can be used as a preventive and/or therapeutic treatment to reduce or inhibit toxic effects of a bacterial infection in an open wound in a subject. The methods are simple and effective and include administering an effective amount of an alkaline phosphatase. Alkaline phosphatases are hydrolase enzymes responsible for removing phosphate groups from many types of molecules, including nucleotides, proteins, and alkaloids. The process of removing the phosphate group is called dephosphorylation. As the name suggests, alkaline phosphatases are most effective in an alkaline environment, with optimal enzyme activity around pH 10. In humans, alkaline phosphatases are present in all tissues throughout the body, but they are particularly concentrated in the liver, kidney, placenta, in growing bone, and in the bile duct. Alkaline phosphatase is released into the blood during injury and during such normal activities as bone growth and pregnancy. Levels of alkaline phosphatase can be measured in routine blood tests.

Intestinal alkaline phosphatase (IAP) is a brush-border enzyme that is expressed exclusively in villus-associated enterocytes of the small intestine and has the primary function of hydrolyzing monophosphate esters, splitting cholesterol and long chain fatty acids, and is associated with the ability to assimilate calcium. It has been shown that IAP is capable of detoxifying lipopolysaccharides (LPS), likely through dephosphorylation of the Lipid-A moiety, the primary source of its endotoxic effects (Beumer et al., J Pharmacol Exp Ther 307:737, 2003).

Alkaline phosphatase from any source can be used. Alkaline phosphatase can be intestinal alkaline phosphatase (IAP), calf intestinal alkaline phosphatase (cIAP), human IAP, bovine IAP, chicken IAP, goat IAP, mammalian alkaline phosphatase, murine alkaline phosphatase, avian alkaline phosphatase, bacterial alkaline phosphatase, fungal alkaline phosphatase, shrimp alkaline phosphatase, placental alkaline phosphatase, secretable placental alkaline phosphatase, placental-like alkaline phosphatase, bone alkaline phosphatase, liver alkaline phosphatase, kidney alkaline phosphatase, germ line alkaline phosphatase, tissue non-specific alkaline phosphatase, modified IAP, recombinant IAP, or any peptide comprising alkaline phosphatase activity. Several exemplary examples of alkaline phosphatase are highlighted below in Table 1.

TABLE 1

Alkaline phosphatase orthologs from seven different species along with their GenBank RefSeq Accession Numbers.

| Species | Nucleic Acid | Amino Acid | GeneID |
|---|---|---|---|
| Bos taurus | NM_173987.1 | NP_776412.1 | 280993 |
| Danio rerio | NM_001014353.1 | NP_001014375.1 | 541539 |
| Drosophila melanogaster | NM_079862.2 | NP_524601.2 | 43671 |
| Escherichia coli BL21(DE3) | cd00016 | YP_003037466.1 | 8156184 |
| Homo sapiens | NM_001631.3 | NP_001622.2 | 248 |
| Mus musculus | NM_001081082.1 | NP_001074551.1 | 76768 |
| Rattus norvegicus | NM_022665.2 | NP_073156.2 | 24197 |
| Schizosaccharomyces pombe | NM_001022665.1 | NP_596739.1 | 2539926 |

Subjects to be Treated

In one aspect of the methods described herein, the subject has, or is at risk of developing, a bacterial infection, e.g., in an open wound, skin, organ. A subject that "has, or is at risk of developing, a bacterial infection in an open wound" is one having one or more symptoms of the condition. Classic symptoms of a bacterial infection include localized redness, heat, swelling and pain. Additional symptoms of a bacterial infection vary greatly and are known to those of skill in the art and include, without limitation, malaise, fever, chills, decreased appetite, dehydration, headaches, tachypnoea, hypoxemia, and diaphoresis. A bacterial infection can be diagnosed by culturing a sample (e.g., tissue, peritoneal fluid, blood, or urine) to determine the bacterial species present in the sample. A subject that is "at risk of developing a bacterial infection in an open wound" is one who has an open wound, or has a planned invasive surgical procedure.

The methods are effective for a variety of subjects including mammals, e.g., humans and other animals, such as laboratory animals, e.g., mice, rats, rabbits, or monkeys, or domesticated and farm animals, e.g., cats, dogs, goats, sheep, pigs, cows, or horses.

Methods of Administration

In general, alkaline phosphatase is mixed with standard pharmaceutically acceptable excipients and/or buffers, and can be administered by irrigation of the open wound. Alkaline phosphatase can be applied topically or locally, directly where its action is desired. As far as efficacy is concerned, irrigation or instillation of the open wound or cavity is preferred. Topical creams, gels, and sprays can also be administered directly to the open wound. An "effective amount" is an amount sufficient to effect beneficial or desired results. For example, a therapeutic amount is one that achieves a desired therapeutic effect, e.g., a reduction or inhibition of toxic effects of a bacterial infection, in an open wound. This amount can be the same or different from a prophylactically effective amount, which is an amount necessary to prevent onset of disease or disease symptoms. An effective amount can be administered in one or more administrations, applications or dosages. A therapeutically effective amount of a composition depends on the composition selected. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the alkaline phosphatase compositions described herein can include a single treatment or a series of treatments. For example, a wound can be irrigated once or a number of times. In the surgical context, the method can include irrigating the wound once or several times, e.g., continuously during surgery. Alkaline phosphatase is available in standard dosage units, and can be administered in dosages from about 1 to 10,000 units, or even higher. These dosages can be administered over one or more hours or days. Testing has shown that this range of dosage is non-toxic and non-immunogenic. Further, alkaline phosphatase can be administered at the same time and length as antibiotic treatment or every day for subjects who have, or at risk of developing, an infection in a body cavity (e.g., peritoneum (e.g., during laparotomy), sinus, oral, ocular, eye) or any open wound or exposed tissue with an established infection or a risk of developing an infection (e.g., chest cavity, sinus, soft tissue abscess, tooth abscess, skin abscess, acne, boils, burns, mucosal tissue).

Pharmaceutical Compositions

The methods described herein include the manufacture and use of pharmaceutical compositions, which include compounds identified by a method described herein as active ingredients. Also included are the pharmaceutical compositions themselves.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral, e.g., irrigation and transdermal (topical) administration.

Methods of formulating suitable pharmaceutical compositions are known in the art, see, e.g., the books in the series *Drugs and the Pharmaceutical Sciences: a Series of Textbooks and Monographs* (Dekker, N.Y.). For example, solutions or suspensions used for parenteral application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or containers made of glass or plastic.

Pharmaceutical compositions suitable for use can include sterile aqueous solutions (where water soluble) or dispersions and sterile powders for the extemporaneous preparation of sterile solutions or dispersion. In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and/or sodium chloride in the composition. Prolonged absorption of the compositions can be brought about by including in the composition an agent that delays absorption, for example, aluminum monostearate and gelatin.

Sterile solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile solutions, the preferred methods of preparation are vacuum drying and freeze-drying, which yield a powder of the active ingredient plus any additional desired ingredient from a previously sterile-filtered solution thereof.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc.

The pharmaceutical compositions can be included in a container, pack, or dispenser together with instructions for administration.

The methods described herein can be used to reduce or inhibit toxic effects of a bacterial infection in an open wound. The open wound can be the result of a surgical procedure (e.g., laparotomy) or a traumatic injury (e.g., laceration, abrasion). The following are examples of the practice of the invention. The examples demonstrate that alkaline phosphatase is useful in reducing or inhibiting toxic effects of a bacterial infection and improving survival rates after surgery.

EXAMPLES

The invention is further described in the following examples, which do not limit the scope of the invention described in the claims.

Example 1

Calf IAP (cIAP) is Active in the Peritoneal Lavage Fluid (PLF)

Figure 1:
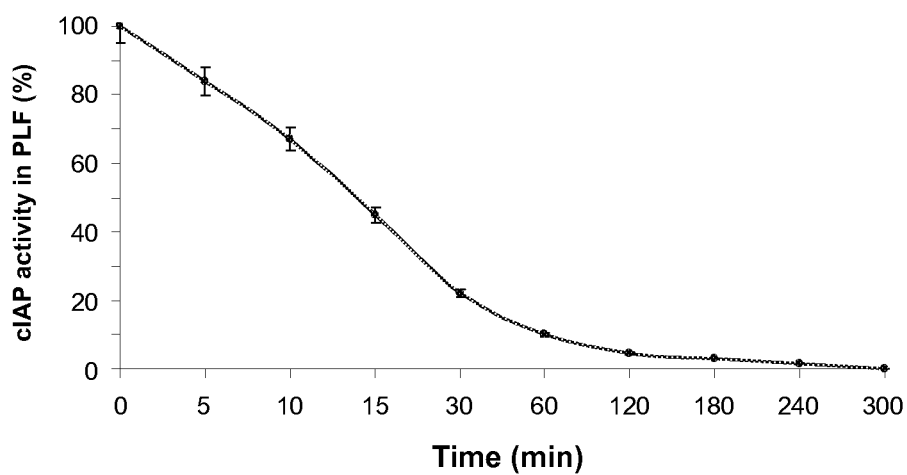
FIG. 1. Elimination curve of calf intestinal alkaline phosphatase (cIAP) from peritoneal lavage fluid (PLF). Each animal of a group (n=3 per group) was injected i.p. 200 units (200 µl) of cIAP and after a specific period of time the animal received an i.p. injection of 5 ml normal saline (NS, 0.9% sodium chloride). One ml of PLF was aspirated and cIAP activity was determined. cIAP activity is expressed as the average percentage (%) of the originally injected amount +/−SD. Note: Peritoneal cavity normally does not contain any fluid. To obtain PLF, an animal was always injected with 5 ml of NS (applicable to all animals of all related experiments described in different figures).

C57BL6 wild-type (WT) mice were given buprenorphine (Reckitt Benckiser Pharmaceutical, USA) 0.05 to 0.1 mg/kg subcutaneously 30 min preoperatively. All mice were anesthetized via inhalation of a mixture of $N_2O$ (nitrous oxide):$O_2$ (oxygen) (1:1 [vol/vol]; 1 to 2 liters/min) and 2.0 to 2.5% isoflurane (Fort Dodge Iowa, USA). During anesthesia the mice were kept on a heating pad at 37° C. All i.p. injections were performed under anesthesia. If the time period between 2 consecutive i.p. injections was more than 10 minutes then the animals were allowed to wake up by stopping inhalation of anesthetic gases. Animals of each group (n=3) received 200 units of cIAP i.p. and after a specific period of time the animal received 5 ml normal saline (NS, 0.9% sodium chloride) i.p. One ml of peritoneal lavage fluid was then aspirated for assaying IAP activity. The results (FIG. 1) show that cIAP maintains approximately 50% of its original activity in the peritoneal cavity after 15 minutes, and detectable amount of IAP activity is observed even after 4 hours.

Example 2

Irrigation with IAP Improves Survival Outcome in a Cecal Ligation and Perforation (CLP) Model Cecal ligation and perforation (CLP) was performed in wild-type (WT) C57BL/6 mice followed by irrigation of the peritoneal cavity with or without calf IAP (cIAP, New England Biolabs, Beverley, Mass.). Mice receiving no cIAP were irrigated with normal saline (NS, 0.9% sodium chloride), which was used as the vehicle to dilute cIAP. Mice were anesthetized as described above (Example 1). Midline laparotomy was performed and the cecum was mobilized and ligated with a 4-0 vicryl suture (Ethicon SUT, USA) just beyond the ileocecal junction and perforated through and through with a 18-gauge needle (Becton Dickinson, USA), constituting the CLP. The abdomen was closed in two layers with a running suture using 6-0 silk (Ethicon SUT, USA). In sham mice, the cecum was manipulated without ligation and puncture. Fluid resuscitation was achieved by administering 1 ml saline subcutaneously. The animals were then treated with i.p. injections of different doses of cIAP (5, 10, 25, and 50 U) depending on the experimental groups (n=12 for each group). The groups receiving an antibiotic had imipenem (500 µg, b.i.d.) as an i.p. injection. The control animals received an i.p. injection of an equal volume of NS (compared to cIAP and/or imipenem volume (200 µl)). Animals were observed daily for 7 days for their survival.

Kaplan-Meier survival curves (FIG. 2A) showed no mortality after sham operation (100% survival) and decreased survival (10%) in the control CLP group (receiving only NS) ($p<0.001$ versus sham). Most control CLP mice died within 48 hours. Peritoneal irrigation with 5 units of cIAP did not show any effect on the 7-day survival rate of CLP mice, however, the survival rate was increased by higher concentrations of cIAP, which ultimately reached its plateau at 25 units (40% vs. 10% survival rate, $p<0.001$ compared to control CLP mice). Compared to a single cIAP injection, multiple injections of cIAP (FIG. 2B) or its co-administration with imipenem (FIG. 2C) did not demonstrate significant additive effects on survival rate.

Example 3

Peritoneal Irrigation with IAP Inhibits Distant Organ Damage in a CLP Model

CLP was performed as described above (Example 2) and the animals were treated +/−cIAP. Animals were sacrificed after 24 hours and blood and lung tissues were collected. To assess any liver damage plasma aspartate aminotransferase (AST) and alanine aminotransferase (ALT) levels were determined, wherein these enzymes are usually increased in the case of any liver damage. Blood from heart was collected in a Microtainer tube containing lithium heparin (Becton Dickinson, Franklin Lakes, N.J.) and centrifuged (1,200×g; 10 min at 4° C.), after which plasma was collected. Activities of AST and ALT were determined by routine laboratory testing.

Hepatocellular damage was assessed by measuring plasma AST (FIG. 3A) and ALT (FIG. 3B) levels. Twenty four hours after CLP, plasma activity of AST was increased in all groups (NS and cIAP) compared to sham groups ($p<0.05$; ANOVA repeated), indicating hepatocellular damage. Treatment with cIAP resulted in reduced release of transaminases throughout the experiments compared to non-treated CLP animals ($p<0.001$; ANOVA repeated). ALT levels showed a pattern similar to that seen for AST, i.e., increased activity after CLP compared to the sham operations ($p<0.001$). Treatment with cIAP did not reduce ALT levels when compared to non-treated CLP animals.

Remote inflammatory response in the lung was assessed by measuring myeloperoxidase (MPO) activity. MPO is an enzyme present in the granules of neutrophils and is an indicator of tissue inflammation. Lung tissue was homogenized in potassium phosphate buffer (50 mM, pH 6.0) with an ultrasonometer (Sonic Dismembrator Model 300, Fisher Scientific, Pittsburgh, Pa.). The homogenate was centrifuged (16,500×g, 20 min at 4° C.), the supernatant was discarded, and the pellet was resuspended in potassium buffer containing 10 mM EDTA and 0.5% hexadecyltrimethylammonium bromide (HTAB) and further homogenized by sonication. The suspension was centrifuged and supernatant was collected. MPO activity was determined by measuring the $H_2O_2$-dependent oxidation of 3,3'5,5' tetramethylbenzidine. The reaction was stopped with glacial acetic acid. Activity was measured immediately by a spectrophotometer as the change in absorbance at 655 nm. Results were expressed as units per milligram (wet weight) of tissue.

Increased MPO activity (FIG. 3C) in the lung was demonstrated 24 hours after CLP compared to sham ($p<0.01$; Mann-Whitney). Twenty-four h after CLP, cIAP-treated groups showed less MPO activity in lung than the non-treated groups ($p<0.05$).

Example 4

Peritoneal Irrigation with IAP Inhibits Local Inflammatory Response in a CLP Model The effect of peritoneal irrigation with cIAP on the local inflammatory response in a CLP model was determined by quantifying proinflammatory cytokines interleukin-6 (IL-6) and tumor necrosis factor-alpha (TNF-α). After performing CLP (Example 2), PLF was collected as described in Example 1. IL-6 and TNF-α levels in PLF were measured by mouse enzyme-linked immunosorbent assay (ELISA) kits (Becton Dickinson, N.J., USA). The plates were read at 450 nm, and cytokine concentrations were estimated by plotting against a standard curve constructed with the recombinant cytokine. Control (no surgery intervention) and sham mice were used as control groups to infer basal cytokine levels.

Twenty four hours after CLP, IL-6 concentrations (FIG. 4A) as well as TNF-α concentrations (FIG. 4B) in PLF were significantly elevated in all CLP groups compared to sham ($p<0.05$, CLP versus sham for PLF IL-6; $p<0.01$, CLP versus sham for TNF-α; ANOVA repeated). IL-6 levels were reduced significantly in cIAP-treated group compared to the non-treated group ($p<0.05$, cIAP-treated CLP versus non-treated sham). Similarly, TNF-α levels in PLF also showed significant decrease after cIAP treatment.

Example 5

Peritoneal Irrigation with IAP Reduces Blood Neutrophil Counts in a CLP Model

Local and systemic neutrophil responses to cIAP-treated CLP animals were evaluated by counting neutrophils in PLF and blood, respectively. Mice were subjected to secondary peritonitis by CLP and were given cIAP (25 Units) or normal saline (NS, 0.9% sodium chloride). Sham treated mice received cIAP or NS. Neutrophil counts per one µl PLF or blood were determined 24 hours after CLP or sham operation.

The number of neutrophils in PLF was significantly increased after CLP ($8\times10^4$/ml vs. $5\times10^3$/ml for CLP and sham, respectively, $p<0.001$) (FIG. 5A). However, no significant difference was observed between peritoneal neutrophil counts in the CLP groups (treated and non-treated CLP).

The number of neutrophils in blood significantly increased in CLP animals compared to sham ($3\times10^5$ vs. $2.5\times10^4$, respectively, $p<0.001$) (FIG. 5B). Neutrophil counts decreased significantly in the blood of cIAP-treated CLP animals compared to non-treated CLP group ($p<0.05$).

Example 6

Peritoneal Irrigation with IAP Apparently Inhibits Local Bacterial Proliferation in a CLP Model The effect of cIAP on local bacterial proliferation in CLP animals was studied by determining the number of bacteria in PLF. CLP was performed following the protocol as described in Example 2 and animals were treated +/−cIAP (25 U, i.p). Twenty-four hours later, PLF was collected following the protocol described in Example 1. PLF was plated in serial log dilutions on *Brucella* agar plate and incubated at 37° C. under aerobic conditions. Colony forming units (CFU) were counted after overnight growth.

While no aerobic bacterial growth was observed in the PLF of sham groups, the number of aerobic bacteria in the PLF of non-treated CLP animals was greatly elevated (approx. $10^{11}$ CFU/ml PLF) (FIG. 6). The number of bacterial counts in cIAP-treated CLP animals was reduced; however, the difference was not significant between the CLP groups.

Example 7

IAP Inhibits LPS-Induced Inflammatory Response in an In Vitro Model

To decipher the molecular mechanisms of how IAP inhibits the inflammatory response in CLP model, cell-based in vitro models were developed to study the effects of IAP on its targets. Gram-negative bacterial lipopolysaccharide (LPS) precipitates inflammatory response via activation of TLR4 pathway and is a known target of IAP. It was decided to study the effects of IAP treatment on bacterial lipopolysaccharides (LPS)-induced production of proinflammatory cytokine interleukin-8 (IL-8) in HT29 cells. HT29 cells were seeded into 12 well plates and grown until 60-70% confluence. LPS (0 to 50 μg/ml, *E. coli* serotype 0111:B4, Sigma, St. Louis, Mo.) were incubated at 37° C. with or without calf IAP (cIAP, 100 units/ml, New England Biolabs, Ipswich, Mass.) for 2 hours. The control LPS solutions (without cIAP) were treated with cIAP buffer only. The solutions were then directly applied to HT29 cells for 24 hours. Media was collected, centrifuged and the supernatant was measured for IL-8 content by ELISA (Biosystems, San Diego, Calif.).

LPS induced IL-8 secretion in HT29 cells in a dose dependent manner (FIG. 7). When LPS was pre-incubated with cIAP, there was nearly complete inhibition of IL-8 secretion by HT29 cells (p<0.5). Therefore, it is probable that cIAP might be inhibiting the LPS-mediated inflammatory response in the CLP model.

Example 8

IAP Inhibits CpG DNA-Induced Inflammatory Response in an In Vitro Model

It was sought to identify more probable targets of IAP. Accordingly, the effect of IAP enzyme on specific bacterial components was examined. The effect of IAP on CpG DNA-induced activation of TLR9 proinflammatory pathway was investigated. HT29 cells were grown as described above (Example 7) and incubated with various amounts of CpG DNA (0-2 μg/ml) pretreated with or without cIAP (100 units/ml). Media was collected, centrifuged, and the supernatant was measured for IL-8 content by ELISA.

CpG DNA induced IL-8 secretion in HT29 cells in a dose dependent manner (FIG. 8). When CpG DNA was pre-incubated with cIAP, there was complete inhibition of IL-8 secretion by HT29 cells (p<0.5). Therefore, it is probable that cIAP might be inhibiting the CpG DNA-mediated inflammatory response in the CLP model. This application reports that the TLR9 ligand, CpG DNA, is a target of IAP.

Example 9

IAP Inhibits Flagellin-Induced Inflammatory Response in an In Vitro Model

The effect of IAP on the bacterial flagellin-induced activation of proinflammatory pathway was investigated. Flagellin (0 to 500 ng/ml, Ultrapure from *Salmonella typhimurium*, Fisher Scientific, Pittsburgh, Pa.) was incubated at 37° C. with or without CIP (100 units/ml) for 16 hours. The solutions were then mixed with undifferentiated THP-1 cells (approximately $10^5$ cells in 250 μl), seeded into 48-well plates, and incubated for 24 hours at 37° C. Media was collected and centrifuged, and the supernatant was assayed for IL-8 content by ELISA.

Flagellin induced IL-8 secretion in THP-1 cells in a dose dependent manner (FIG. 9). When flagellin was pre-incubated with cIAP, there was nearly 80% inhibition of IL-8 secretion by THP-1 cells (p<0.5). Therefore, it is probable that cIAP might also be inhibiting flagellin-mediated inflammatory response in the CLP model. This application reports that IAP inhibits bacterial flagellin induced inflammatory response.

Example 10

IAP Does Not Inhibit Pam3Cys-Induced Inflammatory Response in an In Vitro Model

The effect of IAP on the TLR2 ligand Pam3Cys lipoprotein ((S)-(2,3-bis(palmitoyloxy)-(2RS)-propyl)-N-palmitoyl-(R)-Cys-(S)-Ser(S)-Lys$_4$-OH, trihydrochloride) (EMD Biosciences, Gibbstown, N.J.) was investigated. Approximately $10^6$ THP-1 monocyte cells in 500 μl were seeded into 12-well plates, and differentiated into macrophages using 2 nM phorbol-12-myristate-13-acetate (PMA, Sigma). Pam3Cys (0 to 1,000 ng/ml) was incubated at 37° C. with or without cIAP (100 units/ml) for 2 hours, and then applied to THP-1 cells for 24 hours. IL-8 secretion into media was measured as described above (Example 7).

Pam3Cys did not induce IL-8 secretion in THP-1 cells (FIG. 10), which indicates that Pam3Cys is not a target of IAP and the proinflammatory response in a CLP model is probably not mediated through the TLR2 pathway.

Example 11

IAP Does Not Inhibit TNF-α-Induced Inflammatory Response in an In Vitro Model

The effect of IAP on the TNF-α-induced proinflammatory response was investigated. Approximately $10^6$ HT29 cells in 500 μl were seeded into 12-well plates and incubated at 37° C. for 24 hours. TNF-α (0 to 30 ng/ml) was incubated at 37° C. with or without cIAP (100 units/ml) for 2 hours, and then applied to HT29 cells for 24 hours. IL-8 secretion into media was measured as described above (Example 7).

TNF-α did not induce IL-8 secretion in HT29 cells (FIG. 11), which indicates that TNF-α is not a target of IAP and the proinflammatory response in a CLP model is probably not mediated through the TNFR pathway.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of reducing or inhibiting toxic inflammatory effects of a bacterial infection in a subject undergoing a surgical procedure on the peritoneal cavity, the method comprising:
   selecting a subject having the bacterial infection in the peritoneal cavity; and
   locally irrigating the infected peritoneal cavity with a composition comprising a therapeutically effective amount of an alkaline phosphatase,
   wherein the irrigation reduces or inhibits the inflammation caused by the bacterial infection in the peritoneal cavity of said subject.

2. The method of claim 1, wherein the alkaline phosphatase is an intestinal, placental, tissue non-specific, or germ-line alkaline phosphatase.

3. The method of claim 2, wherein the intestinal alkaline phosphatase is a calf intestinal alkaline phosphatase.

4. The method of claim 2, wherein the intestinal alkaline phosphatase is a human intestinal alkaline phosphatase.

5. The method of claim 1, wherein the subject is a mammal.

6. The method of claim 1, wherein the subject is a human.

7. The method of claim 1, wherein the step of irrigation is performed before, at, or at about the same time as an antibiotic is administered.

8. The method of claim 1, wherein the composition comprises 1 to 10,000 units of alkaline phosphatase.

9. The method of claim 1, wherein the composition comprises alkaline phosphatase at a concentration of 1 to 10,000 units/ml.

* * * * *

UNITED STATES PATENT AND TRADEMARK OFFICE
CERTIFICATE OF CORRECTION

PATENT NO. : 8,932,587 B2  Page 1 of 1
APPLICATION NO. : 13/578103
DATED : January 13, 2015
INVENTOR(S) : Hodin et al.

It is certified that error appears in the above-identified patent and that said Letters Patent is hereby corrected as shown below:

On the title page item [56], insert:

-- Related U.S. Application Data

Provisional Application No. 61/303,942, filed on February 12, 2010. --

Signed and Sealed this
Twenty-fifth Day of August, 2015

Michelle K. Lee
*Director of the United States Patent and Trademark Office*